(12) United States Patent
Carnes (10) Patent No.: US 8,912,897 B2
(45) Date of Patent: Dec. 16, 2014

(54) SYSTEM, METHOD, AND SOFTWARE FOR CONTROLLING ALERT NOTIFICATIONS

(71) Applicant: Tony C. Carnes, Gainesville, FL (US)

(72) Inventor: Tony C. Carnes, Gainesville, FL (US)

(73) Assignee: Covidien LP, Mansfield, MA (US)

( * ) Notice: Subject to any disclaimer, the term of this patent is extended or adjusted under 35 U.S.C. 154(b) by 153 days.

(21) Appl. No.: 13/624,603

(22) Filed: Sep. 21, 2012

(65) Prior Publication Data

US 2014/0085076 A1    Mar. 27, 2014

(51) Int. Cl.
*G08B 23/00*      (2006.01)

(52) U.S. Cl.
USPC .......................... 340/502; 340/506; 340/500

(58) Field of Classification Search
CPC combination set(s) only.
See application file for complete search history.

(56) References Cited

U.S. PATENT DOCUMENTS

2011/0202490 A1*    8/2011    Gawlick ......................... 706/47

* cited by examiner

*Primary Examiner* — Travis Hunnings
(74) *Attorney, Agent, or Firm* — Carter, DeLuca, Farrell & Schmidt, LLP (57) ABSTRACT

A method for controlling alert notifications includes receiving, at an alert notification monitor, notifications from at least one medical device. The method further includes analyzing, at the alert notification monitor, the notifications based on one or more complex triggers to identify at least one triggered notification. The method further includes transmitting the at least one triggered notification.

20 Claims, 4 Drawing Sheets

SYSTEM, METHOD, AND SOFTWARE FOR CONTROLLING ALERT NOTIFICATIONS

TECHNICAL FIELD

The present disclosure relates generally to alert management, and more particularly to a system, method, and software for controlling alert notifications.

BACKGROUND

Patient monitoring systems include alert systems. For example, alert systems may identify simple alert conditions such as a blood pressure exceeding a certain threshold. Present alert systems may generate a large quantity of alarms that may pose a risk of alarm fatigue for clinicians. Forwarding these basic alarms to remote notification systems serves to exacerbate alarm fatigue.

SUMMARY

According to the present disclosure, disadvantages and problems associated with previous techniques for alert management may be reduced or eliminated.

In certain embodiments, a method for controlling alert notifications includes receiving, at an alert notification monitor, notifications from at least one medical device. The method further includes analyzing, at the alert notification monitor, the notifications based on one or more complex triggers to identify at least one triggered notification. The method further includes transmitting the at least one triggered notification.

Certain embodiments of the present disclosure may provide one or more technical advantages. Conventional alert management systems include simple logic to detect alert conditions such as variables crossing thresholds. However, in a scenario where a simple alarm condition continues to beep if a threshold is crossed, sending out a page, text, or email to notify the correct individual(s) of the alarm condition must be carefully controlled to prevent sending hundreds of alert messages for a single patient. For example, consider a scenario where a condition is met and the triggering system checks for conditions once per minute. Assuming the physiologic parameters do not change, there are several logical considerations that present alert systems do not consider, such as: (1) should each person that was identified to receive the notification receive an additional notification every minute; (2) should there be a notification if the physiologic parameters are hovering at the threshold that activates the trigger when they dip below, rise above, and then dip below again on a frequent basis; (3) should the user be notified at every threshold crossing; (4) should the detection be silenced after the condition is identified and if so, for how long; (5) if the first notification is lost, should a second notice be sent; (6) should the notification require acknowledgement; (7) should the acknowledgement include a timed reminder mechanism; (8) should every patient be treated the same way; and (9) should the condition need to hold true for X period of time before a notification is sent? According to certain embodiments of the present disclosure, an alert notification monitor addresses these challenges and allows for the customization of how and when different individuals or groups are notified when a defined trigger condition is activated for identified patients. Thus, the risk of alarm fatigue for clinicians may be reduced.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DESCRIPTION OF EXAMPLE EMBODIMENTS

Figure 1:
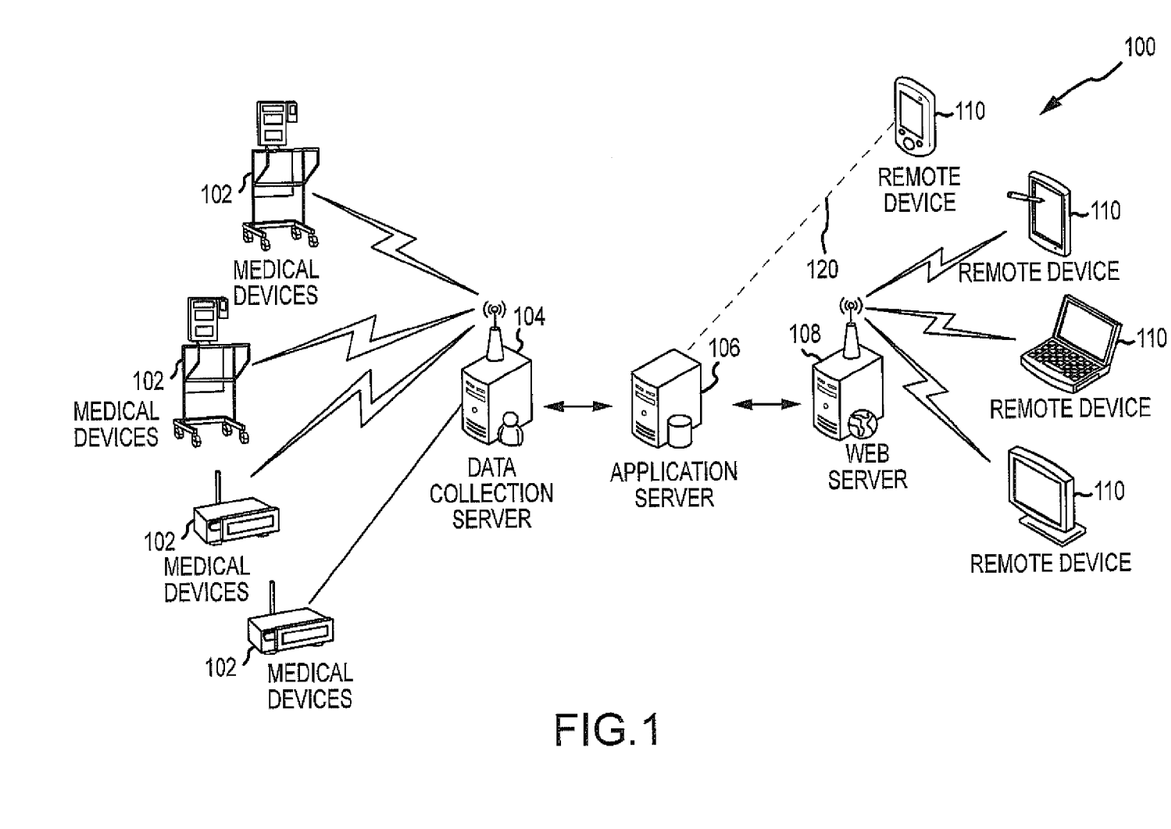
FIG. 1 illustrates an example system for controlling alert notifications, according to certain embodiments of the present disclosure.

FIG. 1 illustrates an example system 100 for controlling alert notifications, according to certain embodiments of the present disclosure. System 100 includes one or more medical devices 102, a data collection server 104, an application server 106, a web server 108, and one or more remote devices 110. According to one embodiment, system 100 is operable to monitor medical devices 102 and transform patient parameters into display parameters. In certain embodiments, medical devices 102 generate patient parameters or store patient parameters input by a user, such as a clinician. Patient parameters may refer to any patient identifiers, medical history, clinician notes, alarm thresholds, alarm events, device settings, measurements of values indicating physiological conditions such as oxygen saturation levels, pulse rates, heart rates, other vital signs, and any other output data from medical devices 102. Each medical device 102 may be connected to data collection server 104, which stores the patient parameters in a database. Application server 106 retrieves the patient parameters from the database and processes the patient parameters into display parameters for web server 108. Remote devices 110 request and receive the display parameters and display the display parameters through a browser, thereby enabling clinicians using the remote devices 110 to view the display parameters in remote locations. As described in more detail below, an alert notification monitor at data collection server 104 includes logic that may receive and analyze patient parameters in the form of notifications received from different medical devices 102.

Although this particular implementation of system 100 is illustrated and primarily described, the present disclosure contemplates any suitable implementation of system 100 according to particular needs. For example, although this implementation of the alert notification monitor is illustrated with remote devices 110 that may be using a web interface or a client/server interface, this disclosure contemplates any suitable implementation of the alert notification monitor. In addition, a component of system 100 may include any suitable arrangement of elements, for example, an interface, logic, memory, other suitable element, or a combination of any of the preceding. An interface receives input, sends output, processes the input and/or output, performs other suitable operation, or performs a combination of any of the preceding. An interface may comprise hardware and/or software.

System 100 may include one or more medical devices 102. Medical devices 102 may be any devices that are used for tracking or treating patients. For example, medical devices 102 may include a ventilator connected to a patient to deliver respiratory therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function. It should be noted that any suitable number of medical devices 102 may be included in system 100. In addition, there may be multiple groups of medical devices 102 in system 100.

According to one embodiment, in addition to performing a medical function, medical devices 102 may generate output data tracked by medical devices 102. For example, the ventilator may generate entries indicating the average volume of air expelled in each breath. The ventilator may generate entries including the parameter settings used by the ventilator and an identification of whether any alarms have been triggered. The ventilator may store the generated entries in local memory and output the entries. In some embodiments, medical devices 102 may generate output data that is related to tracking patient identifications or locations, without necessarily generating data related to a physiological condition. In certain embodiments, medical devices 102 may output data in response to a data request. In certain other embodiments, medical devices 102 may constantly stream output data.

Medical devices 102 may be communicatively coupled to data collection server 104 via a network, according to one embodiment. The network facilitates wireless or wireline communication. The network may communicate, for example, IP packets, Frame Relay frames, Asynchronous Transfer Mode (ATM) cells, voice, video, data, and other suitable information between network addresses. The network may include one or more Serial Networks, local area networks (LANs), radio access networks (RANs), metropolitan area networks (MANS), wide area networks (WANs), all or a portion of the global computer network known as the Internet, and/or any other communication system or systems at one or more locations. In certain embodiments, medical devices may be communicatively coupled to other suitable devices including data collection server 104, application server 106, web server 108, and remote devices 110.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, Macintoshes, workstations, Unix-based computers, server computers, one or more server pools, or any other suitable devices. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may be operable to request patient parameters from a medical device 102 and receive patient parameter sets from the medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106. According to one embodiment of the disclosure, data collection server may receive notifications in the form of patient parameters and transmit triggered notifications.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, Macintoshes, workstations, Unix-based computers, server computers, one or more server pools, or any other suitable devices. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service that runs on a conventional web services platform for transmitting data to web server 108. For example, application server 106 may create webpage data using the patient parameters, and that webpage data is transmitted to web server 108 for display. Application server 106 may maintain an activity log that logs data requests from remote devices 110 to track certain activities performed at the remote devices 110. Application server 106 may create additional data that causes a pop-up window to appear on the mobile device when any of the changed patient parameters are selected. That window may list all of the changed patient parameters and provides a single button through which a user may indicate that that the changed patient parameters have been viewed. If that button is activated, the mobile device may transmit a message to application server 106 and application server 106 may then unflag those patient parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, Macintoshes, workstations, Unix-based computers, server computers, one or more server pools, or any other suitable devices. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive webpage data from application server 106 and transmitted, upon request in certain embodiments, to remote devices 110.

System 100 may include one or more remote devices 110. Remote devices 110 may be any device that provides output to and can receive input from a user, such as a clinician. Each remote device 110 may include one or more computer systems at one or more locations. A remote device 110 may connect to web server 108 or directly to application server 106 as indicated by reference number 120. Each computer system may include any appropriate input devices (such as a keypad, touch screen, mouse, or other device that can accept input), output devices, mass storage media, or other suitable components for receiving, processing, storing, and communicating data. Both the input device and output device may include fixed or removable storage media such as a magnetic computer disk, CD-ROM, or other suitable media to both receive input from and provide output to a user. Each computer system may include a personal computer, workstation, network computer, kiosk, wireless data port, personal data assistant (PDA), one or more processors within these or other devices, or any other suitable processing device.

According to one embodiment, remote devices 110 display one or more web pages hosted by application server 106 and/or web server 108 with patient parameters from medical devices 102. For example, a clinician may activate a browser on remote device 110 and navigate to the web page hosted by web server 108. The browser may render the web page, which includes patient parameters generated by medical devices 102. The web page may provide a summary of all the medical devices 102 under a clinician's responsibility. In addition, the web may display a detailed view that displays specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into display parameters. It will also be understood that this single device may alternatively transmit the display parameters to remote device 110. In certain embodiments, data collection server 104 may be a bedside device that receives patient parameters from medical devices 102.

It will also be understood that the functions may be allocated differently than shown, with application server 106 additionally performing the functions of web server 108 or the functions of data collection server 104. In another embodiment, a single device may receive patient parameters, transform those patient parameters into display parameters, and display the display parameters on a screen.

A user of system 100 may connect many different types of medical devices 102 to examine a combination of patient parameters. The automated capture of patient parameters from medical devices opens up a number of opportunities for improved patient care through automated triggers defined against those parameters. One example of using a complex combination of parameters to detect as specific condition is Resp Rate >16 with 02 Sat <80 and increased Respiratory Effort indicates a likely Obstructed Airway. While many patient conditions may be detected by examining a combination of values crossing thresholds, even more complex conditions can be detected by a decision support system that has the benefit of a retrospective look at previously captured data and the ability to examine those variables is complex ways.

Conventional alert management systems include simple logic to detect alert conditions such as variables crossing thresholds. However, in a scenario where a simple alarm condition that continues to beep if a threshold is crossed, sending out a page, text, or email to notify the correct individual(s) of the complex condition must be carefully controlled to prevent sending hundreds of alert messages for a single patient. For example, consider a scenario where a condition is met and the triggering system checks for conditions once per minute. Assuming the physiologic parameters do not change, there are several logical considerations that present alert systems do not consider, such as: (1) should each person that was identified to receive the notification receive an additional notification every minute; (2) should there be a notification if the physiologic parameters are hovering at the threshold that activates the trigger when they dip below, rise above, and then dip below again on a frequent basis; (3) should the user be notified at every threshold crossing; (4) should the detection be silenced after the condition is identified and if so, for how long; (5) if the first notification is lost, should a second notice be sent; (6) should the notification require acknowledgement; (7) should the acknowledgement include a timed reminder mechanism; (8) should every patient be treated the same way; and (9) should the condition need to hold true for X period of time before a notification is sent?

In certain embodiments of the disclosure, system 100 may include an alert notification monitor to address these concerns. The alert notification monitor may refer to any suitable hardware and/or software operable to be configured to filter patient parameters in the form of notifications received from different medical devices 102 at data collection server 104. Filtering patient parameters may refer to analyzing the received notifications at data collection server 104 based on configuration parameters and transmitting certain triggered notifications based on the analysis to a receiving system. Therefore, the alert notification monitor may communicate true changes in patient status, versus simple threshold crossing, to the correct care providers. Thus, the alert notification monitor may reduce alarm fatigue and ensure that notifications are not so cumbersome as to provoke the care providers to turn off the notification and messaging system. Additional details of example embodiments of the alert notification monitor are discussed below with reference to FIGS. 2-4.

Figure 2:
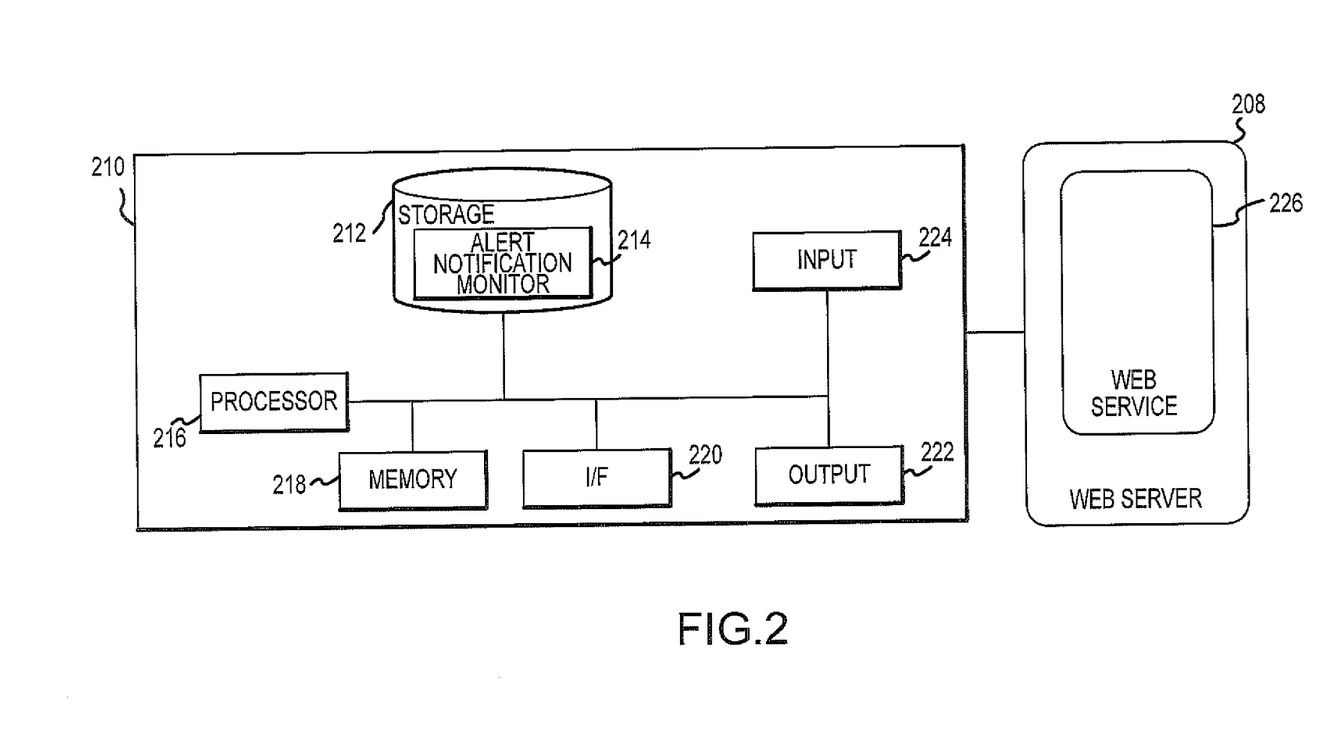
FIG. 2 illustrates an example data collection server and alert notification monitor of the system for controlling alert notifications in FIG. 1, according to certain embodiments of the present disclosure.

FIG. 2 illustrates an example data collection server 210 of the system 100 for configuring communication with medical devices in FIG. 1, according to certain embodiments of the present disclosure. Data collection server 210 may be substantially similar to data collection server 104 of FIG. 1. In FIG. 2, a data collection server 210 is shown as a server communicatively coupled with a web server 208. Web server 208 may be substantially similar to web server 108 of FIG. 1. In other embodiments, data collection server 210 may be communicatively coupled with an application server similar to application server 106 of FIG. 1. Data collection server 210 includes a storage device 212, an alert notification monitor 214, a processor 216, a memory 218, a communication interface (UP) 220, an output device 222, and an input device 224, which are discussed in further detail below. Although this particular implementation of data collection server 210 is illustrated and primarily described, the present disclosure contemplates any suitable implementation of data collection server 210 according to particular needs.

Storage device 212 may include any suitable device operable for storing data and instructions. Storage device 212 may include, for example, a magnetic disk, flash memory, optical disk, or other suitable data storage device.

Alert notification monitor 214 may include any suitable logic embodied in computer-readable media, and when executed, that is operable to be configured to filter patient parameters in the form of notifications received from different medical devices 102 at data collection server 104. For example, alert notification monitor 214 may include logic for receiving, at an alert notification monitor, a plurality of notifications from at least one medical device. The alert notification monitor 214 may analyze, at the alert notification monitor, the plurality of notifications based on one or more complex triggers to identify at least one triggered notification. The alert notification monitor 214 may transmit at least one triggered notification. Additional details of alert notification monitor 214 and triggered notifications are provided below with reference to FIG. 3.

Processor 216 may include any suitable device operable to execute instructions and manipulate data to perform operations for alert notification monitor 214. Processor 216 may include, for example, any type of central processing unit (CPU).

Memory 218 may include any computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for alert notification monitor 214, send output from alert notification monitor 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a Serial, LAN, WAN, or other communication system that allows alert notification monitor 214 to communicate to other devices. I/F 220 may include one or more ports, conversion software, or a combination of any of the preceding.

Output device 222 may include any suitable device operable for displaying information to a user. Output device 222 may include, for example, a video display, a printer, a plotter, or other suitable output device. In certain embodiments, output device 222 may reformat data in any suitable format to be transmitted to other systems.

Input device 224 may include any suitable device operable to input, select, and/or manipulate various data and information. Input device 224 may include, for example, a keyboard, mouse, graphics tablet, joystick, light pen, microphone, scanner, or other suitable input device.

Modifications, additions, or omissions may be made to data collection server 210 without departing from the scope of the disclosure. The components of data collection server 210 may be integrated or separated. Moreover, the operations of data collection server 210 may be performed by more, fewer, or other components. For example, although alert notification monitor 214 is displayed as part of storage device 212, alert notification monitor 214 may be stored in any suitable location, including in another suitable device shown in FIG. 1, and the operations of alert notification monitor 214 may be performed by more than one component. Additionally, operations of data collection server 210 may be performed using any suitable logic. As used in this document, "each" refers to each member of a set or each member of a subset of a set. Further details of an example data collection server 210 and the operations of alert notification monitor 214 are provided below with reference to FIG. 3.

Figure 3:
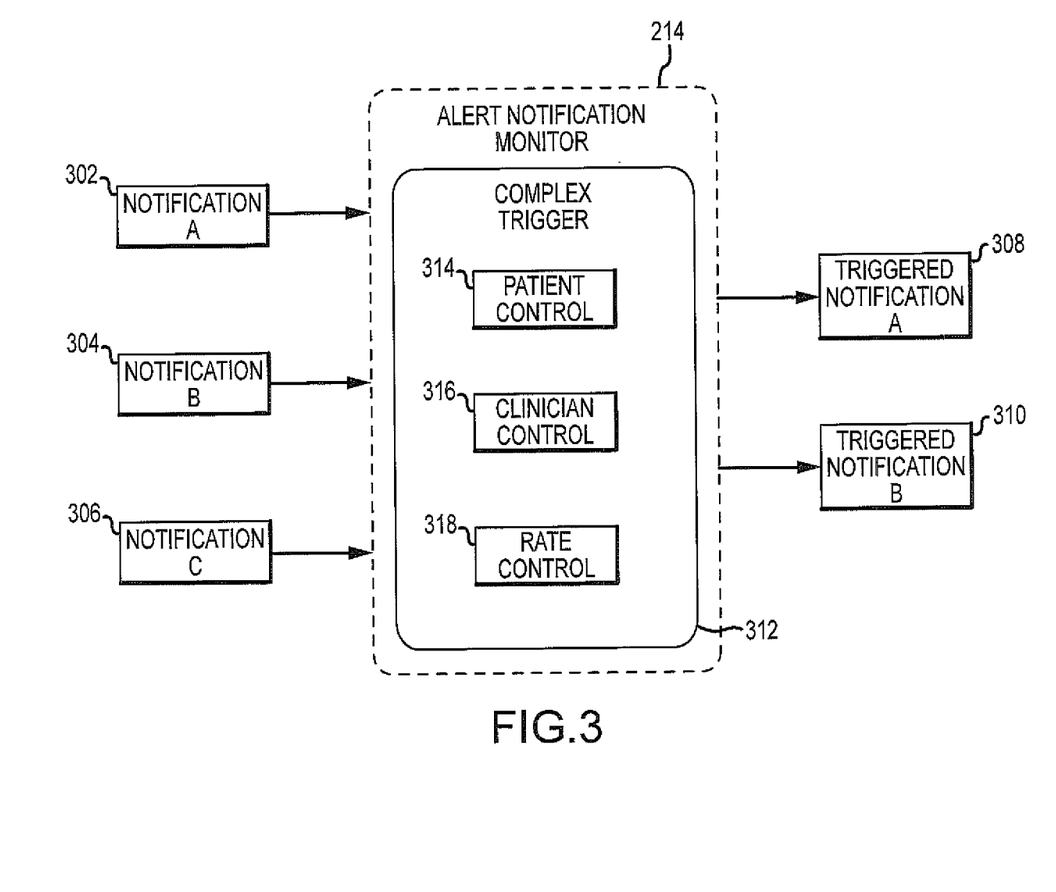
FIG. 3 illustrates one embodiment of an example operation of the alert notification monitor of FIG. 2, according to certain embodiments of the present disclosure.

FIG. 3 illustrates one embodiment of an example operation of alert notification monitor 214 of FIG. 2, according to certain embodiments of the present disclosure. The illustrated embodiment includes a notification A 302, a notification B 304, and a notification C 306, which may include any patient parameters data, such as alarm notifications, generated by respective medical devices, such as medical devices 102 in FIG. 1. According to certain embodiments of the disclosure, notifications 302-306 may be filtered at alert notification monitor 214 and may trigger new notifications, such as triggered notifications 308 and 310 as explained in more detail below.

In certain embodiments, alert notification monitor 214 may include a configurable complex trigger system 312 with a patient control 314, a clinician control 316, and a rate control 318. For example, in certain embodiments of the disclosure, a user may implement patient control 314 to define a set of medical devices that are to be monitored using the one or more complex triggers. In these embodiments, notifications 302-306 may be mapped to a particular patient or patients and triggered notifications 308 and 310 are generated and routed accordingly. As another example, in certain embodiments of the disclosure, a user may implement patient control 314 to define a set of complex trigger conditions that can be selectively activated and deactivated. In these embodiments, notifications 302-306 are analyzed against a set of conditions more complex than traditional threshold level analysis, including complex logic and mathematical equations. If notifications 302-306 satisfy the equations in these example embodiments, then triggered notifications 308 and 310, based on the analysis of notifications 302-306, may be activated and deactivated as appropriate. As another example, in certain embodiments of the disclosure, a user may implement patient control 314 to configure and adjust certain settings/alarm thresholds and notification recipients on a per patient basis. In these embodiments, triggered notifications 308 and 310 are customized per patient, facilitating flexibility for clinicians to define certain threshold alarms for one patient and a different set of thresholds for another patient, as an example.

In certain embodiments of the disclosure, a user may implement clinician control 316 to assign notifications 302-306 to one or more individual clinicians, one or more individual types of clinicians (e.g., all doctors), and one or more groups of clinicians (e.g., nurses on floor one). In these embodiments, if notifications 302-306 are identified to be transferred to a particular group, such as doctors, triggered notifications 308 and 310 may be generated to provide doctors with preferred information and routed accordingly. In other embodiments, a user may implement clinician control 316 to identify a type of triggered notification to be transmitted. In these embodiments, if notification A 302 represents a simple alarm threshold condition but notifications B 304 and notification C 306 represent a serious patient health issue, clinician control 316 may be configured to ignore notification A 302 and identify and transmit triggered notifications 308 and 310 based on notifications B 304 and notification C 306 representing a serious patient health issue, respectively. In other embodiments, a user may implement clinician control 316 to request an acknowledgement message to a triggered notification, such as triggered notifications 308 and 310. In these embodiments, if triggered notifications 308 and 310 are transmitted to a particular clinician, clinician control 316 may transmit a request that the clinician respond or acknowledge triggered notifications 308 and 310. In certain embodiments, clinician control 316 may be configured to refrain from sending additional triggered notifications to a clinician until the clinician responds to a request for acknowledgement of previously transmitted triggered notifications. In other embodiments, a user may implement clinician control 316 to include a specific period of time to wait for an acknowledgement message before resending a triggered notification. In other embodiments, a user may implement clinician control 316 to receive an acknowledgement message with an optional reminder timer component to resend the triggered notification after the specified interval. In certain embodiments, a user may implement clinician control 316 define one or more default values, the one or more default values associated with a particular clinician.

A user may implement rate control 318 to manipulate the output rate of triggered notifications 308 and 310, such as setting a particular time limit to send triggered notifications 308 and 310 based on a frequency of receipt of notifications 302-306, in certain embodiments of the disclosure. In other embodiments, a user may implement rate control 318 to set at least one triggered notification, such as triggered notification 308, to quiescent for a specific period of time. As another example, in certain embodiments, rate control 318 may be configured to override the generic trigger message if desired. As yet another example, in certain embodiments, rate control 318 may be configured with a specific time period to wait before re-checking a trigger condition for a given patient once it has been matched for that patient.

According to one embodiment, alert notification monitor 214 allows end-users to customize notifications and other data that is transmitted to a patient parameter receiving device. In certain embodiments, alert notification monitor 214 provides an interface to allow end-users to address at least the following questions in implementing an intelligent alert system: (1) should each person that was identified to receive the notification receive an additional notification every minute; (2) should there be a notification if the physiologic parameters are hovering at the threshold that activates the trigger so that there is a new notification when they dip below, rise above, and then dip below again on a frequent basis; (3) should the user be notified at every threshold crossing; (4) should the detection be silenced after the condition is identified and if so, for how long; (5) if the first notification is lost, should a second notice be sent; (6) should the notification require acknowledgement; (7) should the acknowledgement include a timed reminder mechanism; (8) should every patient be treated the same way; and (9) should the condition need to hold true for X period of time before a notification is sent? Addressing these concerns may result in a reduction in alarm fatigue because alert notification monitor 214 may communicate true changes in patient status, versus simple threshold crossing, to the correct care providers. In addition, alert notification monitor 214 may ensure that notifications are not so cumbersome as to provoke the care providers to turn off the notification and messaging system.

Modifications, additions, or omissions may be made to complex trigger system 312 without departing from the scope of the disclosure. The operations of complex trigger system 312 may be performed by more, fewer, or other components. Additional details of alert notification monitor 214 and complex trigger system 312 are described below with reference to FIG. 4.

Figure 4:
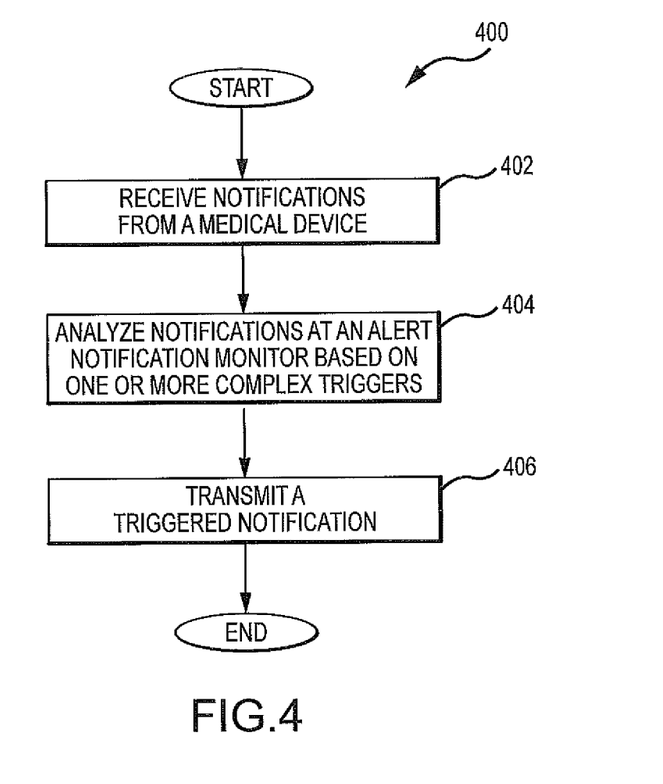
FIG. 4 illustrates an example method for controlling alert notifications, according to certain embodiments of the present disclosure.

FIG. 4 illustrates an example method for configuring communication with medical devices, according to certain embodiments of the present disclosure. The method begins at step 402 where notifications are received from at least one medical device. At step 404, the notifications are analyzed based on one or more complex triggers to identify at least one triggered notification. At step 406, triggered notifications are transmitted. It should be understood that some of the steps illustrated in FIG. 4 may be combined, modified or deleted where appropriate, and additional steps may be added to the flowchart. Additionally, as indicated above, steps may be performed in any suitable order without departing from the scope of the disclosure.

Although the present disclosure has been described with several embodiments, diverse changes, substitutions, variations, alterations, and modifications may be suggested to one skilled in the art, and it is intended that the disclosure encompass all such changes, substitutions, variations, alterations, and modifications as fall within the spirit and scope of the appended claims.

What is claimed is:

1. A method for controlling alert notifications, comprising:
   setting, at an alert notification monitor, a plurality of controls selected from the group consisting of a patient control, a clinician control and a rate control;
   receiving, at the alert notification monitor, a plurality of notifications from at least one medical device;
   analyzing, at the alert notification monitor, the plurality of notifications based on one or more complex triggers to identify at least one triggered notification, the complex triggers incorporating at least one of the plurality of set controls and at least one of the plurality of notifications;
   transmitting the at least one triggered notification; and
   displaying on a display the transmitted triggered notification to a user via a web browser.

2. The method of claim 1, further comprising:
   defining a set of medical devices that are to be monitored using the one or more complex triggers; and
   defining one or more default values, the one or more default values associated with the clinician control and identifying a particular clinician.

3. The method of claim 1, further comprising selectively manipulating the complex triggers for a particular medical device by setting at least one triggered notification to quiescent for a specific period of time.

4. The method of claim 1, wherein the setting of the patient control assigns the plurality of notifications to one or more individuals, one or more individual types, and one or more groups.

5. The method of claim 1, wherein the clinician control specifies a type of triggered notification to be transmitted.

6. The method of claim 1, further comprising requesting an acknowledgement message to the triggered notification.

7. The method of claim 1, wherein the rate control specifies a period of time to wait for an acknowledgement message before resending the triggered notification.

8. A system for controlling alert notifications, comprising:
   at least one medical devices operably connected to a communication network;
   at least one server in communication with the at least one medical device and including, one or more processing units operable to:
      setting, at an alert notification monitor, a plurality of controls selected from the group consisting of a patient control, a clinician control and a rate control;
      receive, at the alert notification monitor, a plurality of notifications from at least one medical device;
      analyze, at the alert notification monitor, the plurality of notifications based on one or more complex triggers to identify at least one triggered notification the complex triggers incorporating at least one of the plurality of set controls and at least one of the plurality of notifications;

transmit the at least one triggered notification; and a display presenting the transmitted triggered notification to a user via a web browser.

9. The system of claim 8, wherein the one or more processing units are operable to:

define a set of medical devices that are to be monitored using the one or more complex triggers; and define one or more default values, the one or more default values associated with the clinician control and identifying a particular clinician.

10. The system of claim 8, wherein the one or more processing units are operable to selectively manipulate the complex triggers for a particular medical device by setting at least one triggered notification to quiescent for a specific period of time.

11. The system of claim 8, wherein the wherein the setting of the patient control assigns the plurality of notifications to one or more individuals, one or more individual types, and one or more groups.

12. The system of claim 8, wherein the clinician control specifies a type of triggered notification to be transmitted.

13. The system of claim 8, wherein the one or more processing units are operable to request an acknowledgement message to the triggered notification.

14. The system of claim 8, wherein the rate control specifies a period of time to wait for an acknowledgement message before resending the triggered notification.

15. Software for controlling alert notifications, the software embodied in a non-transient computer-readable medium and when executed operable to:

present a user interface on a display enabling a user to set, at an alert notification monitor, a plurality of controls selected from the group consisting of a patient control, a clinician control and a rate control;

receive, at an alert notification monitor, a plurality of notifications from at least one medical device;

analyze, at the alert notification monitor, the plurality of notifications based on one or more complex triggers to identify at least one triggered notification, the complex triggers incorporating at least one of the plurality of set controls and at least one of the plurality of notifications;

transmit the at least one triggered notification; and display, via the notification monitor, the transmitted triggered notification to a user in a web browser.

16. The software of claim 15, wherein the software is further operable to:

define a set of medical devices that are to be monitored using the one or more complex triggers; and define one or more default values, the one or more default values associated with the clinician control and identifying a particular clinician.

17. The software of claim 15, wherein the software is further operable to selectively manipulate the complex triggers for a particular medical device by setting at least one triggered notification to quiescent for a specific period of time.

18. The software of claim 15, wherein the setting of the patient control assigns the plurality of notifications to one or more individuals, one or more individual types, and one or more groups.

19. The software of claim 15, wherein clinician control specifies a type of triggered notification to be transmitted.

20. The software of claim 15, wherein the software is further operable to request an acknowledgement message to the triggered notification.

* * * * *